United States Patent [19]

Boltze et al.

[11] 4,324,787

[45] Apr. 13, 1982

[54] 2-OXO-1-PYRROLIDINEACETIC ACID COMPOUNDS AND THEIR MEDICINAL USE

[75] Inventors: Karl-Heinz Boltze; Hans-Dieter Dell, both of Berg. Gladbach; Haireddin Jacobi, Leichlingen, all of Fed. Rep. of Germany

[73] Assignee: Troponwerke GmbH & Co., KG, Cologne, Fed. Rep. of Germany

[21] Appl. No.: 965,374

[22] Filed: Nov. 30, 1978

[30] Foreign Application Priority Data

Dec. 23, 1977 [DE] Fed. Rep. of Germany ....... 2757680

[51] Int. Cl.³ .................. A61K 31/40; A61K 31/495; C07D 207/12; C07D 403/14
[52] U.S. Cl. ................................ 424/250; 260/245.7; 260/326.25; 424/248.54; 424/273 P; 424/274; 544/66; 544/372; 546/281
[58] Field of Search ...................... 260/326.43, 326.25; 548/374; 546/208, 281; 424/256, 274, 263, 273 P; 544/372

[56] References Cited

U.S. PATENT DOCUMENTS

| | | |
|---|---|---|
| 3,459,738 | 8/1969 | Morren ..................... 260/239.3 |
| 3,903,110 | 9/1975 | Freyermuth et al. ......... 260/326.25 |
| 4,056,524 | 11/1977 | Walker ........................ 260/239 BF |
| 4,069,336 | 1/1978 | Lange et al. ................... 260/326.25 |

OTHER PUBLICATIONS

Suchenwirth; Med. Mchr.; vol. 10; pp. 467–469 (1973).
Stegink; Arzneimr Forsch, vol. 22, pp. 975–977 (1972).
Abdow et al., Chem. Abstracts, vol. 90, abstract No. 121147V (1979).
Morrison, R., and R. Boyd, "Organic Chemistry," (3rd ed.) Allyn and Bacon, Inc., Boston, 1974 (pp. 746 and 675).

Primary Examiner—Alton D. Rollins
Attorney, Agent, or Firm—Sprung, Felfe, Horn, Lynch & Kramer

[57] ABSTRACT

The invention relates to 2-oxo-1-pyrrolidineacetic acid compounds, useful as psychopharmacological agents. Also included in the invention are pharmaceutical compositions containing said compounds and methods for the use of said compounds and compositions.

13 Claims, No Drawings

2-OXO-1-PYRROLIDINEACETIC ACID COMPOUNDS AND THEIR MEDICINAL USE

The present invention relates to certain new 2-oxo-1-pyrrolidineacetic acid compounds, to a process for their production and their use as psychopharmacological agents.

According to the present invention there are provided compounds which are 2-oxo-1-pyrrolidineacetic acid derivatives of the following general formula (I)

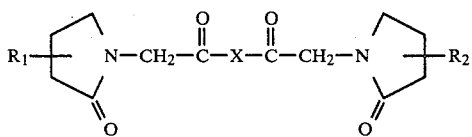

or their salts
in which
$R_1$ and $R_2$ are identical or different and in each case denote a hydrogen atom, one or two lower alkyl groups, one or two lower alkoxy groups, one trifluoromethyl group or one to two halogen atoms and
X denotes a grouping of the general formula

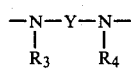

in which
$R_3$ and $R_4$, including the two nitrogen atoms, complete a heterocyclic ring which can also contain one or two hetero-atoms and/or can be substituted by one or more lower alkyl or alkoxy groups or one or more halogen atoms, or
$R^3$ and $R^4$ in each case independently denote a hydrogen atom or a lower alkyl group and
Y denotes an arylene group which is optionally substituted by lower alkyl, alkoxy, halogen atoms or a trifluoromethyl group and which optionally contains a nitrogen atom in the aromatic ring; denotes an alkylenearylenealkylene grouping in which the arylene group is optionally substituted by one or two lower alkyl or alkoxy groups, halogen atoms or trifluoromethyl groups and which optionally contains a nitrogen atom in the aromatic ring; denotes a cycloalkylene group which is optionally substituted by one or two alkyl or alkoxy groups or halogen atoms or a trifluoromethyl group; denotes an alkylenecycloalkylenealkylene grouping in which the cycloalkylene ring is optionally substituted by one or two alkyl or alkoxy groups or halogen atoms; or denotes a straight-chain or branched alkylene grouping which is optionally substituted by a lower alkoxycarbonyl group and in which one or two $CH_2$ groups can be replaced by one or two further hetero-atoms and, in the case where one or both of the hetero-atoms are trivalent, these can also be substituted by lower alkyl groups, where X contains a basic group, the physiologically acceptable salts with acids can be provided. Such acids include, hydrochloric acid, sulfuric acid, acetic acid, succinic acid, pamoic acid, etc.

As used herein the term "lower" in respect of the various groups means such groups having 1 to 4 carbon atoms in their alkyl chain.

Preferred meanings in the definitions of the substituents in the general formula (I) are: the lower alkyl group: a methyl, ethyl, n-propyl or isopropyl group, especially the methyl group; a lower alkoxy group: a methoxy, ethoxy, n-propoxy or isopropoxy group, especially a methoxy group; halogen atoms: chlorine, fluorine and bromine atoms, especially chlorine atoms; a heterocyclic ring: a heterocyclic ring with four to seven ring members, two of which must be nitrogen atoms; examples which may be mentioned are a piperazine ring, pyrazolidine ring, perhydrodiazepine ring or perhydrooxadiazine ring and its various position isomers, especially the piperazine ring; an arylene group: a phenylene or pyridylene group; an alkylene group in an alkylenearylenealkylene grouping or in an alkylenecycloalkylenealkylene grouping: an alkylene group with one to four carbon atoms, which can be straight-chain or branched; examples which may be mentioned are a methylene group, a 1,2-ethylene group, a 1,1-ethylene group, a 1,3-propylene group, a 1,2-propylene group and a 1,4-butylene group; a cycloalkylene group: a cycloalkylene group with four to six carbon atoms, for example, cyclobutylene, cyclopentylene and cyclohexylene groups and their various position isomers, especially a 1,2-cyclohexylene or 1,3- or 1,4-cyclohexylene group; and an alkylene grouping for Y preferably denotes an alkylene grouping with two, or especially nine to twelve, chain members which is optionally substituted by a lower alkoxycarbonyl group, for example, methoxycarbonyl or propoxycarbonyl, and examples which may be mentioned are a 1,2-ethylene group, a 1,3-propylene group, a 1,2-propylene group, a 1,6-hexylene group, a 1,7-heptylene group, a 1,10decylene group, a 3,4-dimethyl-1,6-hexylene group and a 2,2,4-trimethyl-1,6-hexylene group, especially a 1,2-ethylene, 1,2-propylene, 1,6-hexylene and 2,2,4-trimethyl-1,6-hexylene group and a 4-methyl-4-aza-1,6-hexylene group.

The present invention further provides a process for the production of compounds of formula (I) in which a compound of the general formula

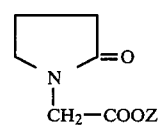

in which
Z denotes a lower alkyl group or an activated ester grouping, is reacted with a compound of the general formula

     (III)

in which
X has the meaning indicated above, optionally in the presence of inert organic solvents and optionally in the presence of a base.

Surprisingly, the 2-oxo-1-pyrrolidineacetic acid derivatives according to the invention exhibit a better activity than psychopharmacological agents, that is to say than comparable active compounds, from the state of the art, for example the known 2-oxo-1-pyrrolidineacetamide (I.N.N.: piracetam). The substances according to the invention thus represent an advance in pharmacy, especially on the basis of their good nootropic action.

If compounds of the general formula (II) in which Z represents a lower alkyl group, such as, for example, the ethyl ester, are used for the reaction, the course of the reaction can be represented by the equation which follows:

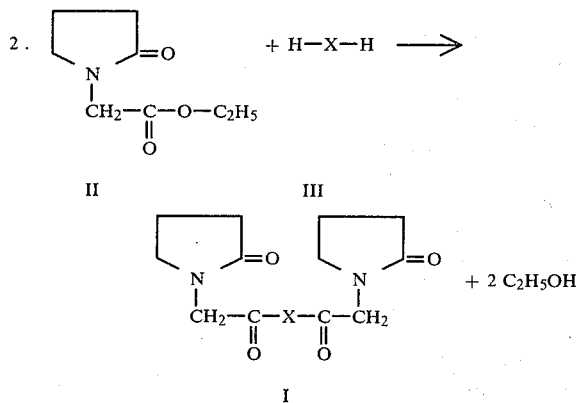

The reaction is appropriately carried out in the presence of diluents. Possible diluents are all the inert organic solvents in which the reactants dissolve. Examples which may be mentioned are alcohols, particularly alkanols, such as methanol, ethanol, propanol or isopropanol, ethers, such as diethyl ether, diglyme or dioxane, or dimethylformamide.

The reaction temperatures can be varied within a substantial range. In general, the reaction is carried out at the boiling point of the particular solvent.

The temperature and solvent also depend on the reactivity of the particular amine of the general formula (III). In the case of very inactive amines, it has proved appropriate to use an activated ester, for example the trichlorophenyl ester, instead of the ethyl ester of the general formula (II).

In this case also, diluents are appropriately used. Possible diluents are all the organic solvents in which the reactants at least partly dissolve. Examples which may be mentioned are methylene chloride, chloroform, dioxane, diglyme, morpholine, pyridine, dimethylformamide, ethyl acetate and methyl acetate, dimethylformamide has proved particularly suitable.

The reaction temperatures are between $-20°$ C. and $+60°$ C., preferably between $-5°$ C. and $+30°$ C. The reaction is generally carried out under normal pressure.

In carrying out the process according to the invention, 0.5 mol of the particular amine of the general formula (III) is employed per mol of the particular compound of the general formula (II).

The reaction time varies and is between five and twenty hours, depending on the reaction temperature.

Working up is generally carried out by evaporation of the solvent and chromatography of the residue on silica gel from a suitable solvent system.

The 2,4,5-trichlorophenyl ester of 2-oxo-1-pyrrolidineacetic acid has not hitherto been described in the literature. It is formed in a known manner by reacting 2,4,5-trichlorophenol with the above-mentioned acid in a suitable solvent in the presence of dicyclohexylcarbodiimide.

In detail, new active compounds which may be mentioned are: 1,2-bis-(2-oxo-1-pyrrolidineacetamido)-ethane, 1,6-bis-(2-oxo-1-pyrrolidineacetamido)-hexane, 1,4-bis-(2-oxo-1-pyrrolidineacetyl)-piperazine, N-methyl-N,N'-bis-(2-oxo-1-pyrrolidineacetyl)-ethylenediamine, N,N'-dimethyl-N,N'-bis-(2-oxo-1-pyrrolidineacetyl)-ethylenediamine, 4-methyl-1,7-bis-(2-oxo-1-pyrrolidineacetyl)-4-aza-1,7-diaminoheptane, 2,2,4-trimethyl-1,6-bis-(2-oxo-1-pyrrolidineacetyl)-1,6-diaminohexane, 1,4-bis-(2-oxo-1-pyrrolidineacetamido)-cyclohexane, α,α'-bis-(2-oxo-1-pyrrolidineacetamido)-m-xylene and 1,2-bis-(2-oxo-1-pyrrolidineacetyl)-1,2-propylenediamine.

The present invention also includes the use of the active compounds according to the invention and the use of pharmaceutical formulations which contain one or more active compounds according to the invention in medicine.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite;

(i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. pepper-mint oil and eucalyptus oil) and sweetening agents (e.g. saccharin).

The pharmaceutical compositions according to the invention generally contain from 0.1 to 99.5, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules.

Some of these forms may be made up for delayed release of the active ingredient. Some, such as capsules, include a protective envelope which renders the portions of the medicament physically discrete and coherent.

The preferred daily dose for administration of the medicaments of the invention is 50 mg to 5 g, preferably 500 to 2.5 g, of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously intravenously), or rectally, preferably orally. Preferred pharmaceutical compositions and medicaments are therefore those adapted for administration such as oral administration. Administration in the method of the invention is preferably oral administration.

In general it has proved advantageous to administer amounts of from 1 mg to 100, preferably 10 to 50 mg/kg of body weight per day to achieve effective results. An individual administration preferably contains the active compound in amounts of from 0.5 to 50, preferably 3 to 30, mg/kg of body weight. Nevertheless, it can at times be necessary to deviate from those dosage rates, and in particular to do so as a function of the nature and body weight of the warm-blooded animal to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

2-Oxo-1-pyrrolidineacetic acid derivatives of the general formula (I) in which $R_1$ and $R_2$ in each case denote a hydrogen, fluorine or chlorine atom or a methyl or methoxy group, X denotes a grouping

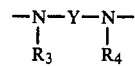

in which $R_3$ and $R_4$, including the two nitrogen atoms, complete a heterocyclic ring with 5, 6 or 7 ring members, $R_3$ and $R_4$ in each case denote a hydrogen atom or a methyl group and Y denotes a phenylene or pyridylene group, denotes an alkylenearylenealkylene grouping in which the alkylene groups contain 1 or 2 carbon atoms and the arylene group denotes a phenylene or pyridylene group, denotes a cycloalkylene group with 5, 6 or 7 ring members, or denotes a straight chain or branched alkylene group with 2 to 9 carbon atoms, which is optionally substituted by an ethoxycarbonyl group and in which a CH$_2$ group is optionally replaced by N-alkyl (with 1 or 2 carbon atoms), are of particular interest.

The preparation of compounds of the present invention is illustrated by the following Examples.

EXAMPLE 1

1,2-Bis-(2-oxo-1-pyrrolidineacetamido)-ethane 17.1 g (0.1 mol) of ethyl 2-oxo-1-pyrrolidineacetate and 3 g (0.05 mol) of 1,2-ethylenediamine are dissolved in 30 ml of isopropanol and the solution is boiled for 8 hours, moisture being excluded. The precipitate (6.5 g) which separates out on cooling is chromatographed on silica gel from the solvent system methanol/NH$_4$OH (9:1).

Melting point: 212°–213° C., yield: 5.75 g (35% of theory)

C$_{14}$H$_{22}$N$_4$O$_4$ (310.35) calculated: C 54.18%, H 7.14%, N 18.05%; found: C 54.11%, H 7.01%, N 17.98%.

2.9 g of 2-aminoethyl-(2-oxo-1-pyrrolidine)acetamide p-aminobenzoate, melting point 149°–150° C., are also obtained, as an oily compound, from the chromatogram described above.

EXAMPLE 2

1,6-Bis-(2-oxo-1-pyrrolidineacetamido)-hexane 10 g (0.06 mol) of ethyl 2-oxo-1-pyrrolidineacetate and 3.4 g (0.03 mol) of 1,6-diaminohexane are dissolved in 5 ml of absolute methanol and the solution is boiled for 19 hours, moisture being excluded. Ether is added to the solution and the precipitate which separates out is filtered off. The product is purified by chromatography on silica gel from methanol:water (100:25).

Melting point: 122° C., yield: 8.2 g (74% of theory). C$_{18}$H$_{30}$N$_4$O$_4$ (366.47) calculated: C 58.99%, H 8.25%, N 15.29%; found: C 58.98%, H 8.36%, N 15.18%.

EXAMPLE 3

1,4-Bis-(2-oxo-1-pyrrolidineacetyl)-piperazine

The title compound is obtained from 10 g (0.06 mol) of ethyl 2-oxo-1-pyrrolidineacetate and 2.5 g (0.03 mol) of piperazine, analogously to Example 2.

Melting point: 292° C., yield: 1.1 g (11% of theory). C$_{16}$H$_{24}$N$_4$O$_4$ (336.40) calculated: C 57.12%, H 7.19%, N 16.65%; found: C 57.13%, H 7.31%, N 16.40%.

EXAMPLE 4

N-Methyl-N,N'-bis-(2-oxo-1-pyrrolidineacetyl)-ethylenediamine

The title compound is obtained from 8.55 g (0.05 mol) of ethyl 2-oxo-1-pyrrolidineacetate and 1.85 g (0.025 mol) of N-methylaminoethylamine, analogously to Example 2.

It is an oily product of n$_D^{54}$ 1.5205;

yield: 1 g (40% of theory). C$_{15}$H$_{24}$N$_4$O$_4$ (324.39) calculated: C 55.54%, H 7.45%, N 17.2%; found: C 55.23%, H 7.75%, N 17.28%.

EXAMPLE 5

N,N'-Dimethyl-N,N'-bis-(oxo-1-pyrrolidineacetyl)-ethylenediamine 12.88 g (0.04 mol) of 2,3,5-trichlorophenyl 2-oxo-1-pyrrolidineacetate are dissolved in 200 ml of absolute dimethylformamide and the solution is kept for 15 hours, finally at room temperature. After evaporating off the solvent, the residue is extracted by washing with petroleum ether, the insoluble constituent is chromatographed on silica gel from methanol/water (20:7.5) and the oily eluate is again chromatographed on silica gel with the solvent system methanol/water/acetic acid (20:7.5:2.5).

Melting point: 149° C., yield: 4.5 g (69% of theory). C$_{16}$H$_{26}$N$_4$O$_4$ (338.42) calculated: C 56.78%, H 7.74%, N 16.55%; found: C 56.88%, H 7.68%, N 16.67%.

EXAMPLE 6

4-Methyl-1,7-bis-(2-oxo-1-pyrrolidineacetyl)-4-aza-1,7-diaminoheptane 8.55 g (0.05 mol) of ethyl 2-oxo-1-pyrrolidineacetate and 3.63 g (0.025 mol) of methyldi-(3-aminopropyl)-amine are boiled in 5 ml of absolute methanol for 22 hours, moisture being excluded. After evaporating off the solvent, the residue is chromatographed on silica gel from the solvent system methanol/water/ammonia (80:20:1). The eluate is evaporated, the residue from the solution is taken up in methylene chloride, active charcoal is added, the mixture is shaken and filtered, the filtrate is evaporated and the residue is dried. It is an oily product of n$_D^{54}$ 1.5135.

Yield: 5.2 g (52.5% of theory)

C$_{19}$H$_{33}$N$_5$O$_4$ (448.57) calculated: C 52.54%, H 7.69%, N 15.61%; found: C 52.29%, H 8.10%, N 15.98%.

EXAMPLE 7

2,2,4-Trimethyl-1,6-bis-(2-oxo-1-pyrrolidineacetyl)-1,6-diaminohexane 8.55 g (0.05 mol) of ethyl 2-oxo-1-pyrrolidineacetate and 3.95 g (0.025 mol) of 2,2,4-trimethyl-1,6-diaminohexane are boiled in 5 ml of absolute methanol for 22 hours, moisture being excluded. After evaporating off the solvent, the residue is chromatographed on silica gel from methanol/water (80:30). Chromatography is then carried out a second time from methanol/water/acetic acid (20:7.5:2.5), and finally the water and the acetic acid are removed by chromatography on aluminium oxide. The product is syrupy with n$_D^{54}$ 1.5095.

Yield: 5.8 g (57% of theory)

C$_{21}$H$_{36}$N$_4$O$_4$.0.5 H$_2$O (417.55) calculated: C 60.40%, H 8.93%, N 13.41%; found: C 60.35%, H 9.09%, N 13.41%.

EXAMPLE 8

1,4-Bis-(2-oxo-1-pyrrolidineacetamido)-cyclohexane 9.66 g (0.03 mol) of 2,4,5-trichlorophenyl 2-oxo-1-pyrrolidineacetate are dissolved in 150 ml of dimethylformamide, and a solution of 1.71 g (0.015 mol) of 1,4-diaminocyclohexane in 20 ml of dimethylformamide is added at −5° C., moisture being excluded. After leaving the mixture to stand at 0° C. for a quarter of an hour, and at room temperature for a further three hours, the solvent is evaporated off, the residue is treated with acetone and the precipitate which has separated out is filtered off, washed with ether and dried.

Melting point: 294° C. (methanol/ether), yeidl: 4.1 g (75% of theory).

C$_{18}$H$_{28}$N$_4$O$_4$ (364.45) calculated: C 59.32%, H 7.74%, N 15.37%; found: C 59.24%, H 7.81%, N 15.34%.

EXAMPLE 9

α,α'-Bis-(2-oxo-1-pyrrolidineacetamido)-m-xylene

The title compound is obtained by reacting 12.8 g (0.04 mol) of 2,4,5-trichlorophenyl 2-oxo-1-pyrrolidineacetate and 2.72 g (0.02 mol) of α,α'-diamino-m-xylene, analogously to Example 8, and purifying the product from methanol on silica gel.

Melting point: 169°–170° C., yield: 6.6 g (88% of theory).

$C_{20}H_{26}N_4O_4$ (386.46) calculated: C 62.15%, H 6.78%, N 14.49%; found: C 62.14%, H 6.84%, N 14.53%.

EXAMPLE 10

1,2-Bis-(2-oxo-1-pyrrolidineacetyl)-1,2-propylenediamine

The title compound is obtained from 12.88 g (0.04 mol) of 2,4,5-trichlorophenyl 2-oxo-1-pyrrolidineacetate and 1.48 g (0.02 mol) of 1,2-diaminopropane, analogously to Example 9.

Melting point: 147°–148° C., yield: 4.3 g (66.5% of theory).

$C_{15}H_{24}N_4O_4$ (324.39) calculated: C 55.54%, H 7.45%, N 17.27%; found: C 55.58%, H 7.57%, N 17.31%.

EXAMPLE 11

2,6-Bis-(2-oxo-1-pyrrolidineacetamido)-pyridine 0.05 mol of 2-(2-oxo-1-pyrrolidine)-acetyl chloride is dissolved in 200 ml of methylene chloride and reacted with 0.25 mol of 2,6-diaminopyridine at −5° C. in the presence of triethylamine, moisture being excluded. After leaving the mixture to stand at +10° C. for one hour, the solvent is evaporated off in vacuo, the residue is treated with acetone and the product is then purified by chromatography over silica gel (methanol:water; 100:25).

Melting point: 240°–242° C., yield: 58% of theory

EXAMPLE 12

2,6-Bis-(2-oxo-1-pyrrolidineacetamido)-hexanoic acid ethyl ester 0.02 mol of L-2,6-diamino-hexanoic acid ethyl ester is dissolved in 10 ml of water and reacted with 0.02 mol of 4-ethyl-morpholine, as an acid-binding agent, and with 0.04 mol of 2,4,5-trichlorophenyl 2-oxo-1-pyrrolidineacetate in 80 mol of dioxane at 20° C. The reaction solution is left to stand at 22° for 20 hours and the solvent is then evaporated off. The residue is taken up in a mixture of ethanol and dichloroethane (1:1) and purified by chromatography over silica gel.

Yellowish syrup, yield: 48% of theory

Specific rotation $[\alpha]_D^{20} - 10.55°$ (c=2 cm).

EXAMPLE 13

2,6-Bis-(2-oxo-1-pyrrolidineacetamidomethyl)-pyridine 0.02 mol of 2,4,5-trichlorophenyl 2-oxo-pyrrolidineacetate is dissolved in 50 ml of dimethylformamide and reacted with a solution of 0.01 mol of 2,6-diaminomethylpyridine in 20 ml of dimethylformamide, at −5° C., whilst stirring and with the exclusion of moisture. After leaving the reaction solution to stand at room temperature for three hours, it is warmed to 60° C. for 2 hours, the solvent is then evaporated off, ether is added to the residue and the crystals which precipitate are filtered off. Melting point: 149° C., yield 57% of theory Starting compound

2,4,5-trichlorophenyl 2-oxo-1-pyrrolidineacetate 84.8 g of 2-oxo-1-pyrrolidineacetic acid and 128.5 g of 2,4,5-trichlorophenol are dissolved in 1,500 ml of methylene chloride, 138.75 g of dicyclohexylcarbodiimide are slowly added at 0° C. and the mixture is stirred at 20° C. for three hours. The urea which has precipitated is then filtered off, the solvent is evaporated off and the residue is recrystallised from ethyl acetate.

Melting point: 128° C., yield: 188 g.

$C_{12}H_{10}Cl_3NO_3$ (322.58) calculated: C 44.68%, H 3.12%, Cl 32.9%, N 4.34%; found: C 44.66%, H 3.14%, Cl 32.94% N 4.49%.

Among the new salts of the invention, those salts that are pharmaceutically acceptable are particularly important and are preferred.

The new free compounds of the general formula (I) and their salts can be interconverted in any suitable manner; methods for such interconversion are known in the art.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to a warm-blooded animal is converted in the animal's body to the active compound.

What is claimed is:

1. A 2-oxo-1-pyrrolidineacetic acid compound of the formula (I)

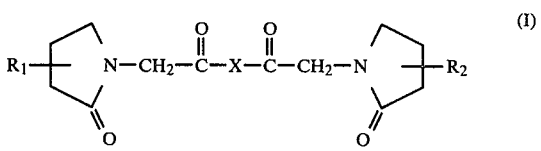

or its physiologically acceptable salts
in which
R₁ and R₂ are identical or different and in each case denote a hydrogen atom, one or two lower alkyl groups, one or two lower alkoxy groups, one trifluoromethyl group or one or two halogen atoms and
X denotes a grouping of the formula

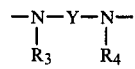

in which
R₃ and R₄, including the two nitrogen atoms and Y, complete a piperazine or pyrazolidine ring which is unsubstituted or substituted by one or more $C_1$–$C_3$ alkyl or $C_1$–$C_3$ alkoxy groups or one or more halogen atoms, or
R₃ and R₄ in each case independently denote a hydrogen atom or a lower alkyl group and
Y denotes phenylene or pyridylene optionally substituted by lower alkyl, lower alkoxy, halogen atoms or a trifluoromethyl group; denotes an alkylenearylene-alkylene grouping in which arylene is phenylene or pyridylene and is optionally substituted by one or two lower alkyl or lower alkoxy groups, halogen atoms or trifluoromethyl groups; a cycloalkylene group with 4 to 6 ring members which is optionally substituted by one or two alkyl or alkoxy groups or halogen atoms or a trifluoromethyl group; or denotes a straight-chain or branched alkylene grouping which is optionally substituted by a lower alkoxycarbonyl group and in which one CH$_2$ group can be replaced by nitrogen, said nitrogen atom being unsubstituted or substituted by lower alkyl.

2. A compound according to claim 1, in which R$_1$ and R$_2$ in each case denote a hydrogen, fluorine or chlorine atom or a methyl or methoxy group, X denotes a

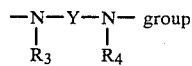
group in which R$_3$ and R$_4$, including the two nitrogen atoms and Y, complete a piperazine or pyrazolidine, ring, or R$_3$ and R$_4$ in each case denote a hydrogen atom or a methyl group and Y denotes (1) a phenylene or pyridylene group, (2) an alkylenearylenealkylene grouping in which the alkylene groups contain 1 or 2 carbon atoms and the arylene group denotes a phenylene or pyridylene group, (3) cycloalkylene group with 4 to 6 ring members, or (4) a straight-chain or branched alkylene group with 2 to 9 carbon atoms, which is optionally substituted by an ethoxycarbonyl group and in which a CH$_2$ group is optionally replaced by N-alkyl (with 1 or 2 carbon atoms), or its physiologically acceptable salts.

3. A compound of claim 1 or its salts in which R$_1$ and R$_2$ are identical or different in each is a hydrogen atom, or two lower alkyl groups or lower alkoxy groups, one trifluoromethyl group or one or two halogen atoms; X is a grouping of the general formula

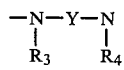

in which R$_3$ and R$_4$ taken together with the two nitrogen atoms and Y form a piperazine or pyrazolidine ring; or R$_3$ and R$_4$ in each case independently denote a hydrogen atom or a lower alkyl group and Y denotes a phenylene group or a pyridylene group which are optionally substituted by one or two lower alkyl or lower alkoxy groups, halogen atoms or trifluoromethyl groups; or Y denotes a cycloalkylene group with 4 to 6 ring members or a straight-chain or branched alkylene group with 2 to 9 carbon atoms which is optionally substituted by a lower alkoxy-carbonyl group and in which one CH$_2$-group can be replaced by a nitrogen atom which itself is unsubstituted or substituted by lower alkyl.

4. A compound of claim 1 wherein,

R$_1$ and R$_2$ are hydrogen

Y, R$_3$ and R$_4$ taken together with the nitrogen atoms form a piperazine ring or R$_3$ and R$_4$ independently are hydrogen or methyl and Y is phenylene, xylylene, cyclohexylene, pyridylene or alkylene of 2–12 carbon atoms, optionally substituted by ethoxycarbonyl or interrupted by a nitrogen atom.

5. A pharmaceutical composition containing as an active ingredient a nootropically effective amount of a compound according to claim 1 in admixture with an inert diluent.

6. A pharmaceutical composition containing as an active ingredient a nootropically effective amount of a compound according to claim 1 in the form of a sterile or physiologically isotonic aqueous solution.

7. A composition according to claim 6 containing from 0.5 to 95% by weight of the said active ingredient.

8. A medicament in dosage unit form comprising an effective amount of a compound according to claim 1 together with an inert pharmaceutical carrier.

9. A medicament of claim 8 in the form of tablets, pills, dragees, capsules, ampoules, or suppositories.

10. A method of combating disorders of the brain function in warm-blooded animals which comprises administering to the animals a nootropically effective amount of an active compound according to claim 1 either alone or in admixture with a diluent or in the form of a medicament.

11. A method according to claim 10 in which the active compound is administered in an amount of 50 mg to 5 g per kg body weight per day.

12. A method according to claim 11 in which the active compound is administered in an amount of 500 mg to 2.5 g per kg body weight per day.

13. A method according to any of claims 10 or 11 in which the active compound is administered orally.

* * * * *